United States Patent [19]

Rose, Jr.

[11] Patent Number: 5,180,479
[45] Date of Patent: Jan. 19, 1993

[54] ELECTRO-KINETIC SEPARATION WITH ENLARGED INPUT MIXING CAPILLARY

[75] Inventor: Donald J. Rose, Jr., Mountain View, Calif.

[73] Assignee: Hewlett-Packard Company, Palo Alto, Calif.

[21] Appl. No.: 649,778

[22] Filed: Feb. 1, 1991

[51] Int. Cl.$^5$ .............................................. G01N 27/26
[52] U.S. Cl. ............................ 204/299 R; 204/180.1; 204/183.3
[58] Field of Search ............... 204/180.1, 183.3, 299 R

[56] References Cited

U.S. PATENT DOCUMENTS

| | | | |
|---|---|---|---|
| 4,676,897 | 6/1987 | Kuze et al. | 204/299 R |
| 4,936,974 | 6/1990 | Rose et al. | 204/299 R |
| 4,994,165 | 2/1991 | Lee et al. | 204/299 R |
| 5,110,431 | 5/1992 | Moring | 204/299 R |

OTHER PUBLICATIONS

Andrew J. Weber et al., "Peroxyoxalate Chemiluminescence Detection with Capillary Liquid Chromatography", *Analytical Chemistry*, vol. 59, No. 10, May 15, 1987, pp. 1452-1457.

M. Van Vliet et al., "Post-Column Reaction Detection for Open-Tubular Liquid Chromatography Using Lazar-Induced Fluorescence" *Journal of Chromatography*, 363, 1986, pp. 187-197.

Donald J. Rose et al., "Post-Capillary Fluorescence Detection in Capillary Zone Electrophoresis Using o-Phthaldialdehyde", *Journal of Chromatography*, 447, 1988, pp. 117-131.

Takao Tsude et al., "Post-Column Detection for Capillary Zone Electrophoresis", *Journal of Chromatography*, 456, 1988, pp. 375-381.

M. Arthur Moseley et al., "Design of an On-Line Coaxial Continuous Flow Interface".

Jos S. M. de Wit et al., "Design of a Coaxial Continuous Flow Fast Atom Bombardment Probe".

*Primary Examiner*—John Niebling
*Assistant Examiner*—David G. Ryser

[57] ABSTRACT

A capillary zone electrophoresis chemical analysis system provides for rapid, non-turbulent, post-separation diffusional mixing of sample effluent with a fluorogenic labeling reagent, permitting sensitive detection of well-defined sample component zones. A power supply and opposing electrodes establish a field which induces charge-related differential electrophoretic migration to define component zones. A flared input of a mixing capillary defines an annular gap between the separation capillary and the mixing capillary. The effluent of the separation capillary is mixed with the labeling reagent, which is introduced through the annular gap. Thus, fluorescence labeling is effective with minimum zone broadening. This system combines the high resolving power of CZE separation with the sensitivity of labeled fluorescence detection to attain an improved system for analyzing biological samples.

5 Claims, 5 Drawing Sheets

ELECTRO-KINETIC SEPARATION WITH ENLARGED INPUT MIXING CAPILLARY

BACKGROUND OF THE INVENTION

The present invention relates to analytical systems and, more particularly, to chemical analysis instruments in which sample components are separated by differential migration rates through a narrow-bore capillary. A major objective of the present invention is to provide for both high-resolution component separation and high-sensitivity detection of separated components of proteins and comparable complex species.

Advances in biotechnology have relied in large part on techniques of chemical analysis. Biotechnology has provided techniques for manufacturing life-supporting medicines and other products which would otherwise be in short supply if natural sources had to be relied upon. In addition, entirely new medical products are in development which may arrest and cure heretofore untreatable diseases. Biotechnology promises new products for agriculture which will feed the world's expanding populations and which will enhance the ability of famine-prone countries to sustain themselves.

Chemical analysis of the proteins found in biological samples generally involves the separation of the samples into components for identification and quantification. Capillary zone electrophoresis (CZE) is one of a class of methods in which the different components are moved within a narrow-bore capillary at respective and different rates so that the components are divided into distinct zones. The distinct zones can be investigated within the capillary or outside the capillary by allowing the components to emerge from the capillary for sequential detection.

In CZE, a sample is introduced at an input end of a longitudinally extending capillary and moved toward an output end under the influence of an electric field. This influence combines two electro-kinetic effects: electro-osmotic flow and electrophoretic migration.

Electro-osmotic flow results from charge accumulation at the capillary surface due to preferential adsorption of anions from the electrolyte solution that fills the capillary bore. The negative charge of the anions attracts a thin layer of mobile positively charged electrolyte ions that accumulate adjacent to the inner surface. The thin layer of mobile positively charged electrolyte ions is pulled toward the negative electrode, dragging the bulk of the sample along with it. Thus, the electro-osmotic flow results in a mean flow of sample components from the positive electrode toward the negative electrode.

Superimposed on this electro-osmotic flow is electrophoretic migration, the well-known motion of charged particles in an electric field. The electrolyte solution acts as the medium that permits the electric field to extend through the capillary between the electrodes. Positively charged molecules are attracted toward the negative electrode so they flow faster than the mean flow determined by the electro-osmotic flow. Negatively charged molecules are attracted toward the positive electrode. For the negatively charged particles, the electrophoretic flow components opposes the, generally larger, electro-osmotic flow component. The result is that negatively charged particles flow toward the negative electrode, but more slowly than the mean flow.

As a result of the combined electrophoretic and electro-osmotic flow, each sample component moves through the capillary separation column at a rate dependent on its species-specific charge. Due to the differential flow rates, the components separate after a sufficiently long migration through the separation capillary. An appropriately selected and arranged detector can detect these zones seriatim as they pass. Components can be identified by the time of detection and can be quantified by the corresponding detection peak height and/or area. In some cases, the bands can be collected in separate containers for a distinct identification and/or quantification process.

There are several types of detectors used to detect proteins in capillary separation systems. Ultraviolet absorbance (UV) detectors are among the most common. In addition, chemiluminescence, refractive index, and conductivity detectors have been used. All these methods lack the sensitivity required to detect many peaks obtained in CZE protein analysis.

High sensitivity is required because the quantity of the total sample is limited, and the detector must be capable of detecting components that make up only a fraction of the total sample. Limitations on sample quantity stem from the requirement that the sample be dissolved in electrolyte and that the concentration of the sample be low enough to avoid perturbation of the electrical field which would lead to distortion of the separated component zones. The sample quantity is further limited by the capillary bore diameter and by the necessity of confining the sample initially to a relatively short longitudinal extent. The initial sample extent governs the minimum zone breadth and thus the ability of the detector to resolve similarly charged sample components.

The detector must be able to detect small quantities of the component in each sample zone. A UV detection system faced with low concentrations and a short illumination path across a capillary typically yields a poor signal-to-noise ratio. Other detection methods are similarly limited. Thus, while CZE is effective in separating protein components, it has been difficult to find a sufficiently sensitive detector for identifying and quantifying the separated components.

Fluorescence detection has been applied in conjunction with liquid chromatography (LC), a class of alternative component separation techniques. In liquid chromatography, a liquid mobile phase ushers components through a capillary at different rates related to the components' partitioning between the mobile phase and a stationary phase. Zones thus form as a function of partitioning ratios. The zones can be illuminated and the resulting fluorescence detected. Few proteins can be detected with sufficient sensitivity using their intrinsic fluorescence. However, labeling reagents can be used to enhance protein fluorescence. A major advantage of using fluorescence detection is that the increased sensitivity required by small sample quantities can be achieved by using very intense illumination. Thus, fluorescence detection used with labeling reagents promises to enhance the ability to identify and quantify sample components.

Unfortunately, liquid chromatography is not well suited for high resolution separation of proteins. While partitioning ratios differ among components, the molecules of any one component at any time are divided between the mobile phase and the stationary phase, and thus move at different rates relative to each other. Despite averaging effects over the length of the capillary, sufficient zone broadening is induced by the partitioning to prevent high resolution separation of protein components. Since its only source of zone broadening is longitudinal diffusion, CZE represents an approximately ten-fold improvement in zone-breadth-limited resolution over liquid chromatography.

Fluorescence detection of proteins is not generally used in conjunction with CZE for a number of reasons. As indicated above, few proteins can be detected with sufficient sensitivity using their intrinsic fluorescence. Pre-separation fluorescence labeling is incompatible with CZE since it causes same-species molecules to have different charges. Thus, one component separates into multiple peaks, rendering detections virtually uninterpretable. Furthermore, sensitivity problems are compounded because each peak represents only a fraction of a sample component.

Post-separation labeling involves the introduction of a fluorogenic labeling reagent after separation and before detection. Post-separation mixing is addressed by Van Vliet et al., "Post-Column Reaction Detection for Open-Tubular Liquid Chromatography Using Laser-Induced Fluorescence," *Journal of Liquid Chromatography*, Vol. 363, pp. 187-198, 1986. This article discloses the use of a Y-connector for introducing reagent into the effluent of a separation capillary. One problem with the Y-connector is the inevitable turbulence that occurs as the streams merge at an oblique angle. The turbulence stirs the sample stream, severely broadening the component zones. This broadening can be tolerable in a low-resolution system, but not in a high-resolution CZE system.

Post-separation mixing is also addressed by Weber et al. in "Peroxyoxalate Chemiluminescence Detection with Capillary Liquid Chromatography" in *Analytical Chemistry*, Vol. 59, pp. 1452-1457, 1987. Weber et al. disclose the use of a Teflon tube to convey the separated sample components emerging from a liquid chromatography capillary, packed with silica particles to the interior of a mixing capillary. An annular gap between the Teflon tube and the mixing capillary is used to introduce the chemiluminescence reagent coaxially of the sample emerging from the narrower (0.2 mm) Teflon tube and into the (0.63 mm) mixing capillary. Turbulence is minimized since the reagent flow is fast enough to define a sheathing flow confining the sample.

A major limitation of the approach of Weber et al. is that chemiluminescence cannot generally be employed in protein component detection. Many proteins cannot activate chemiluminescence reagents. Moreover, the approach does not provide the required sensitivity for those proteins that do activate the reagents.

Another problem with the approach of Weber et al. is that the sheathing flow causes mixing to occur slowly. Sufficient mixing of the chemiluminescence reagent with sample components thus requires a relatively long mixing interval and large mixing volume, resulting in substantial zone broadening. This zone broadening significantly impairs resolution. While this zone broadening may be tolerable in the relatively low resolution liquid chromatography system disclosed, it would negate the advantages of a high-resolution CZE system.

Another approach is to narrow the effluent end of the separation capillary so that it can fit inside the input end of the mixing capillary. When a tapered separation capillary is fit inside a constant bore size mixing capillary, an annular gap is created between the capillaries. Fluorescent labeling reagent can then be introduced through the annular gap. However, this approach has limitations. For optimal fit, the mixing capillary has an inner bore diameter greater than the inner bore diameter of the separation capillary. When the sample exits from the smaller bore and enters the larger bore, the sample spreads, leading to broadened sample zone widths.

Other approaches have involved the introduction of fluorescent labeling reagents through apertures in capillary walls. In a CZE separation system, an aperture or other inhomogeneity in the capillaries defining the sample path can cause field perturbations, which can interfere with electro-osmotic and other electro-kinetic effects. At a minimum, these perturbations cause zone broadening, but can even partially or completely impair electro-kinetic movement of sample components.

In summary, CZE provides a separation technique which affords the resolution required for the analysis of complex proteins, but lacks a sufficiently sensitive compatible detection technique. Fluorescence detection provides a desirable level of sensitivity, but the required labeling has not been workable in the CZE context. What is needed is a system that combines the resolving power of CZE with the detection sensitivity available with fluorescence-labeled proteins.

SUMMARY OF THE INVENTION

In accordance with the present invention, an electrokinetic capillary chemical separation system comprises a mixing capillary with an enlarged input end. The output end of a separation capillary is inserted into this enlarged input end, defining an annular gap between the separation output end and the mixing input end. A fluorogenic labeling reagent, other fluid capable of aiding detection, can be introduced into the effluent of the separation capillary through this annular gap. The reagent and sample mix within a mixing section of the mixing capillary.

A power supply and associated electrodes are arranged to provide an electric field through the separation and mixing capillaries. Sample introduction means are provided for introducing a sample into the separation capillary. For example, a reservoir with sample solution can be provided. The input of the separation capillary can be inserted into the sample solution. An electric field applied along the separation and mixing capillary can be used to urge sample solution into the input end of the separation capillary. Subsequently, the input end of the separation capillary can be introduce into an electrolyte. At this point, no more sample is introduced, but sample already introduced begins to migrate and separate into its components.

A suitable detector arranged downstream of the mixing section can be used to detect sample peaks. In a preferred realization of the present invention, a non-fluorescent fluorogenic reagent is mixed with the component peaks eluting from the separation capillary. In this case, a fluorescence detector can be used with an intense ultraviolet light source and a photomultiplier detector.

The output end of the separation capillary can be tapered to better conform to the shape of the input end of the mixing capillary so that mixing is rapid and minimally turbulent. By minimizing turbulence and providing rapid mixing, zone broadening is minimized. Strong illumination can enhance fluorescence and thus compensate for the small sample volume of a small diameter separation capillary. Background noise is minimized by using a fluorogenic reagent that does not fluoresce unless combined with sample components.

The Einstein equation for diffusion, $\bar{x} = (2Dt)^{\frac{1}{2}}$, establishes practical limits on the diameters of the separation and mixing capillaries required for sufficiently rapid diffusional mixing. The inner diameter of the mixing section of the mixing capillary should not exceed 100 μm and the maximum inner diameter of the separation capillary should not exceed 250 μm so that mixing times are limited to about a second. Preferably, the separation capillary has a constant bore size. Also preferably, the bore size of the mixing capillary, except at the input end, is constant and approximately the same as, or somewhat larger than, that of the separation capillary.

A bore diameter of 100 μm or less permits the electro-osmotic flow to act uniformly across the capillary cross section and minimizes convection-induced zone broadening. Diameters smaller than 100 μm can provide greater electrical resistance between electrodes 104 and 120. The greater resistance permits greater voltage for a given current. A higher voltage is desirable because it induces more rapid migration. More rapid migration results in less zone broadening due to diffusion (which is time-related) without compromising peak separation. It is necessary to limit current to avoid boiling of the electrolyte.

The present invention provides for high resolution separation techniques, such as chemical zone electrophoresis. The reagent introduction approach minimizes band broadening due to mixing. Furthermore, the bore diameter for most of the length of the mixing capillary can be the same as that of the separation capillary, avoiding sample spreading due to bore size differences. Sensitivity is maximized by using a fluorogenic reagent so that detector sensitivity can be enhanced simply by increasing detector illumination intensity. The noise floor can be minimized by selecting a non-fluorescent reagent so that reagent only contributes to the fluorescence detection signals when combined with sample components. These and other features and advantages of the present invention are apparent from the description below with reference to the following drawings.

DESCRIPTION OF THE PREFERRED EMBODIMENTS

Figure 1:
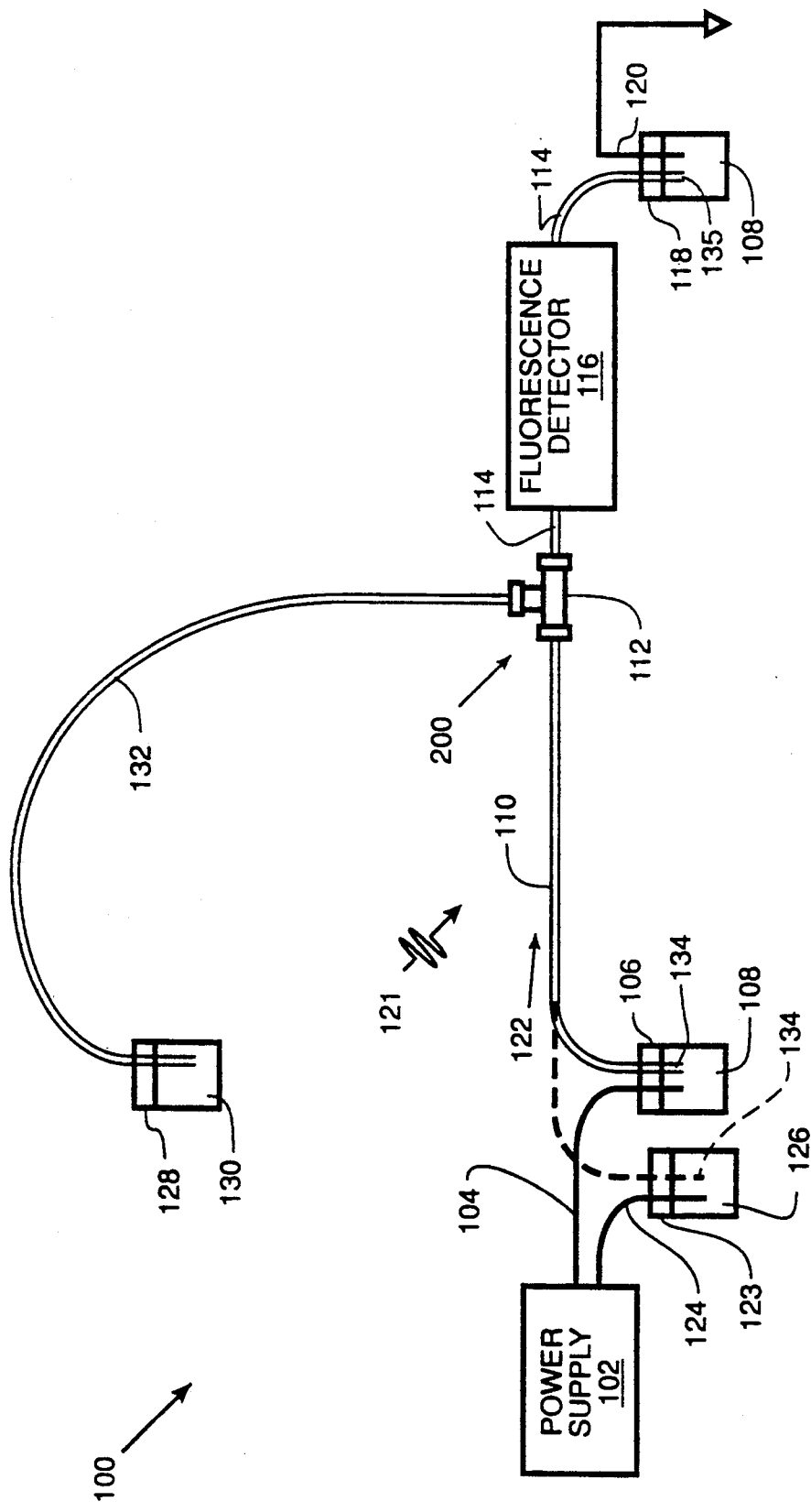
FIG. 1 is a schematic view of a capillary zone electrophoresis system in accordance with the present invention.

A capillary zone electrophoresis (CZE) system 100 comprises power supply 102, a first positive electrode 104, a first electrolyte reservoir 106 containing a solution of electrolyte 108, a separation capillary 110, a mixing tee 112, a mixing capillary 114, a fluorescence detector 116, a second electrolyte reservoir 118 also containing electrolyte 108, and a grounding electrode 120. Separation capillary 110, mixing tee 112, and mixing capillary 114 constitute a sample path means 121 that defines a sample path 122.

Electrolyte 108, which fills most of separation capillary 110 and mixing capillary 114, serves as a medium for the electric field that extends along sample path 121 between electrodes 104 and 120. The same electrolyte is used as a solvent carrier for the biological sample to be analyzed. A sample reservoir 123, with a second positive electrode 124 inserted therein, contains a sample solution 126. A reagent reservoir 128 contains o-phthaldialdehyde (OPA) reagent 130 that is directed along a reagent capillary 132 to mixing tee 112 for mixing with the effluent of separation capillary 110 within mixing capillary 114. Reagent flow can controlled by adjusting the height of reagent reservoir 128 relative to mixing tee 122.

Sample solution 126 can be introduced into separation capillary 110 via input end 134. Input end 134 is first placed into sample reservoir 123 while an output end 135 of mixing capillary 112 is in second electrolyte reservoir 118. Power supply 102 establishes an electric field from positive electrode 124, through separation and mixing capillaries 110 and 114, to grounding electrode 120. As electrolyte is drawn downstream toward grounding electrode 120 by electro-osmotic flow, sample solution 126 is drawn into separation capillary 110 at its input end 134. Power supply 102 is turned off at the end of time interval required to introduce the appropriate amount of sample solution 126, which is typically about 2 nanoliters.

Input end 134 of separation capillary 110 is then inserted into the first electrolyte reservoir 108, to establish the configuration illustrated in FIG. 1. Power supply 102 again establishes an electric field that induces an electro-osmotic flow. Superimposed on this flow are relative electrophoretic migration rates that depend on the magnitudes and signs of molecular charges. The result is that each sample component moves at a characteristic rate through separation capillary 110 into mixing capillary 114 and each passes by fluorescence detector 116 at a respective time.

Fluorescence detector 116 illuminates labeled sample components within mixing capillary 114 using a well-focused, high-intensity ultraviolet light, such as a mercury xenon arc lamp or an ultraviolet laser. Detector 116 includes a photo-multiplier tube which converts the resulting fluorescence intensity into a photo-current that is used to obtain an intensity versus time output.

Figure 2:
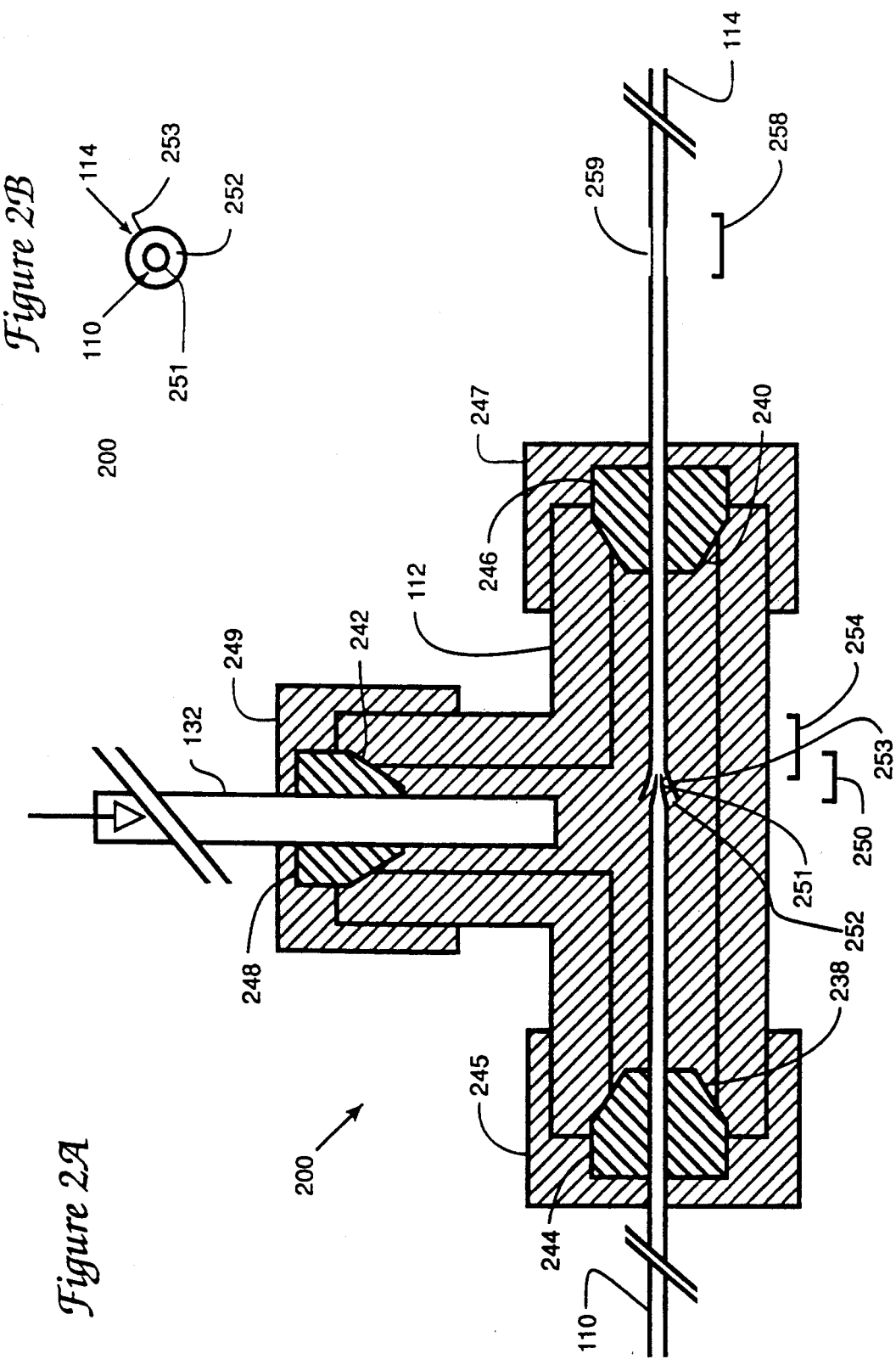
FIG. 2A is a schematic sectional view of a mixing junction of the system of FIG. 1.
FIG. 2B is a cross-sectional view of the mixing junction of FIG. 2A.

Post-separation labeling is performed at junction 200, detailed in FIG. 2A. Stainless steel mixing tee 112 has two in-line ports 238 and 240, and an orthogonal port 242. Separation capillary 110 is supported by a first ferrule 244 where it extends through first in-line port 238, while the mixing capillary 114 is supported by second ferrule 246, where it extends through second in-line port 240. Reagent capillary 132 extends through orthogonal port 242 where it is secured by a third ferrule 248. Ferrules 244, 246 and 248 are held in place by respective caps 245, 247 and 249.

Fused silica reagent capillary 132 has an inner diameter of 200 μm, an outer diameter of 325 μm, and a length of 70 cm. Taking the direction of sample flow to define a longitudinal downstream direction, then, in accordance with the present invention, separation capillary 110 extends into mixing capillary 114 so that the two are longitudinally overlapping, defining overlap region 250, and preferably concentric. Overlap region 250 includes a tapered output end 251 of separation capillary 110 and a flared input end 253 of mixing capillary 114.

In overlap region 250, an annular gap 252 is defined between separation output end 251 and mixing input end 253, as shown in cross section in FIG. 2B. Annular gap 252 provides fluid communication between reagent capillary 132 and a mixing section 254, shown in FIG. 2A, of mixing capillary 114 near output end 251 of separation capillary 110. This permits fluorogenic reagent 130 to mix with separation capillary effluent after sample component separation. After sufficient mixing, sample illumination and fluorescence detection can occur through a window 259 of a detection section 258., located downstream of mixing section 254.

Figure 3:
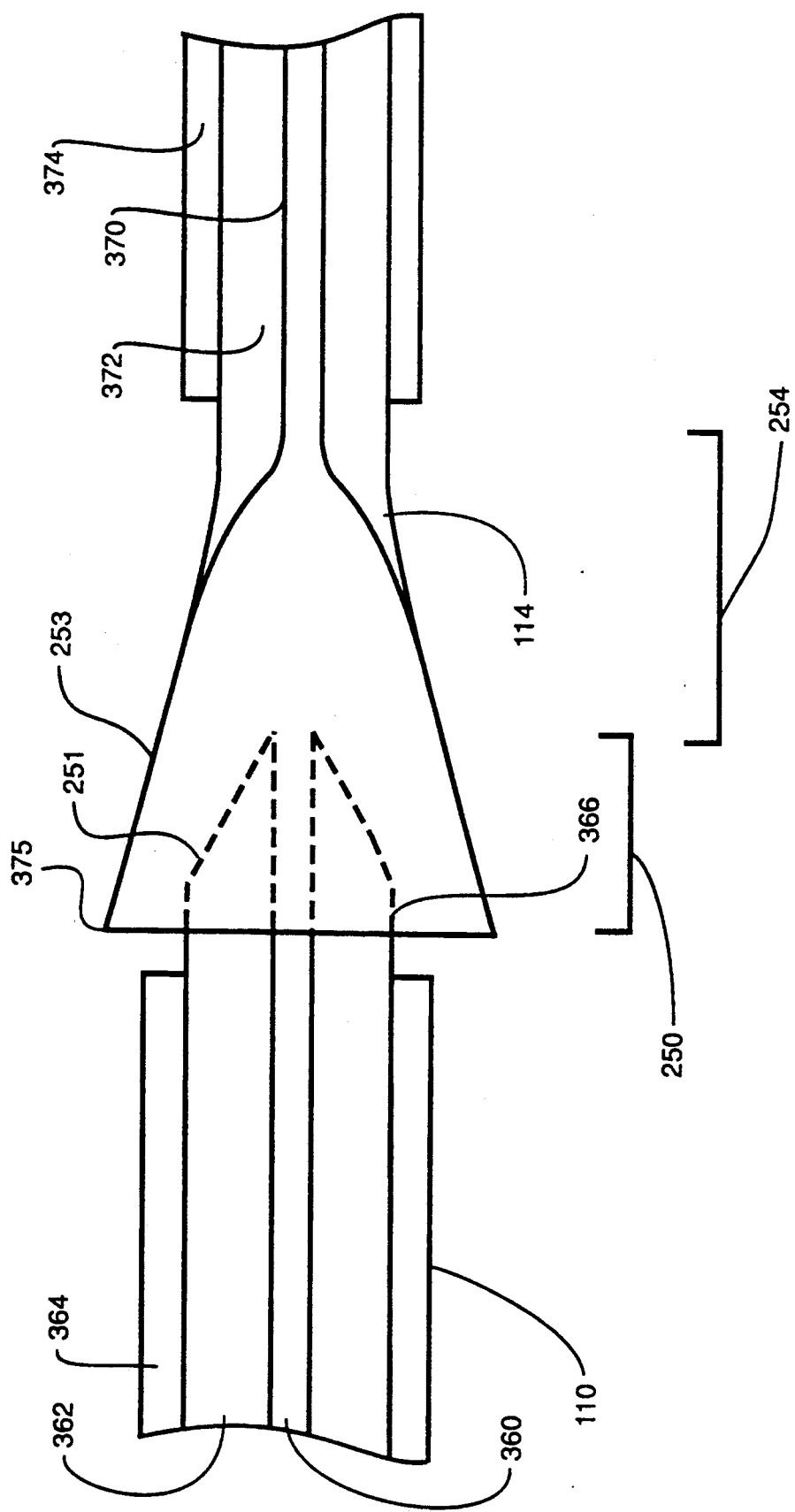
FIG. 3 is a schematic illustration of overlapping ends of a separation capillary and a mixing capillary in the mixing junction of FIG. 2A.

The coaxial interface between separation output end 251 and mixing input end 253 is shown in greater detail in FIG. 3. The separation capillary 110 includes a central electrophoretic capillary bore 360, 25 μm in diameter, a fused silica wall 362, extending radially from the 25 μm diameter to a 125 μm outer diameter. Separation capillary wall 362 is coated with a protective polyimide plastic coating 364, which extends to an outermost diameter of 150 μm. Coating 364 has been removed from exposed section 366 at and near separation output end 251. Output end 251 is tapered to an outer diameter of 30 μm, which is slightly greater than the constant inner diameter of separation capillary 110.

Separation capillary 110 was formed by modifying a commercially available capillary tube having the dimensions of separation capillary tube 110. The modification begins by stripping the coating over what will become exposed section 366 and then etching end 251 in a stirred bath of concentrated (48%) hydrofluoric acid. During etching, water is forced through separation capillary 110 toward the etchant solution to prevent interior etching.

Mixing capillary 114 has a bore 370 that is flared near input end 253. Mixing capillary 114 has an inner diameter of 150 μm at the input end and 25 μm at the effluent end. A wall 372 defining bore 370 of the silica mixing capillary 114 has an outer diameter of 120 μm over most of the capillary length, reaching a maximum diameter of 250 μm at enlarged input end 253. Mixing capillary 114 was formed by modifying a commercially available capillary tube having the dimension of mixing capillary 114 as shown in FIG. 3 where the plastic coating 374 is in place. The modification begins by stripping the coating over the section that becomes input end 253. The capillary is sealed off at one end, and a syringe is used to pressurize it to several atmospheres.

A section of the capillary is heated so that the section is expanded radially by the internal pressure. The capillary is rotated over a gas flame to ensure that the expansion is uniform around the circumference of the capillary. The expansion defines a bulb or cell along the length of the capillary. The expansion time is controlled so that the bulb has the diameter desired of the input end of mixing capillary 114. The bulb is then cut with a quartz cleaving tool. The resulting flared end on the capillary is then smoothed with a drummel tool, completing mixing capillary 114.

Alternatively, a miniature glass lathe as described in U.S. patent application Ser. No. 07/319,460, assigned to the same assignee as the instant application, can be used. The glass lathe supports the capillary at both ends and spins the capillary under a $CO_2$ laser. In a carefully time-controlled manner, the laser sweeps across the area that becomes the input end for the mixing capillary. This causes the bore to expand. As above, the resulting cell is then cut with a quartz cleaving tool, and the resulting enlarged end on the capillary is then smoothed with a drummel tool.

Fused silica is used for all three capillaries 110, 114, and 132, due to its flexibility, transparency, and electrical insulation. Detection window 259 can be formed by burning off a 1-2 cm section of polyimide coating 374 from detection section 258.

Figure 4:
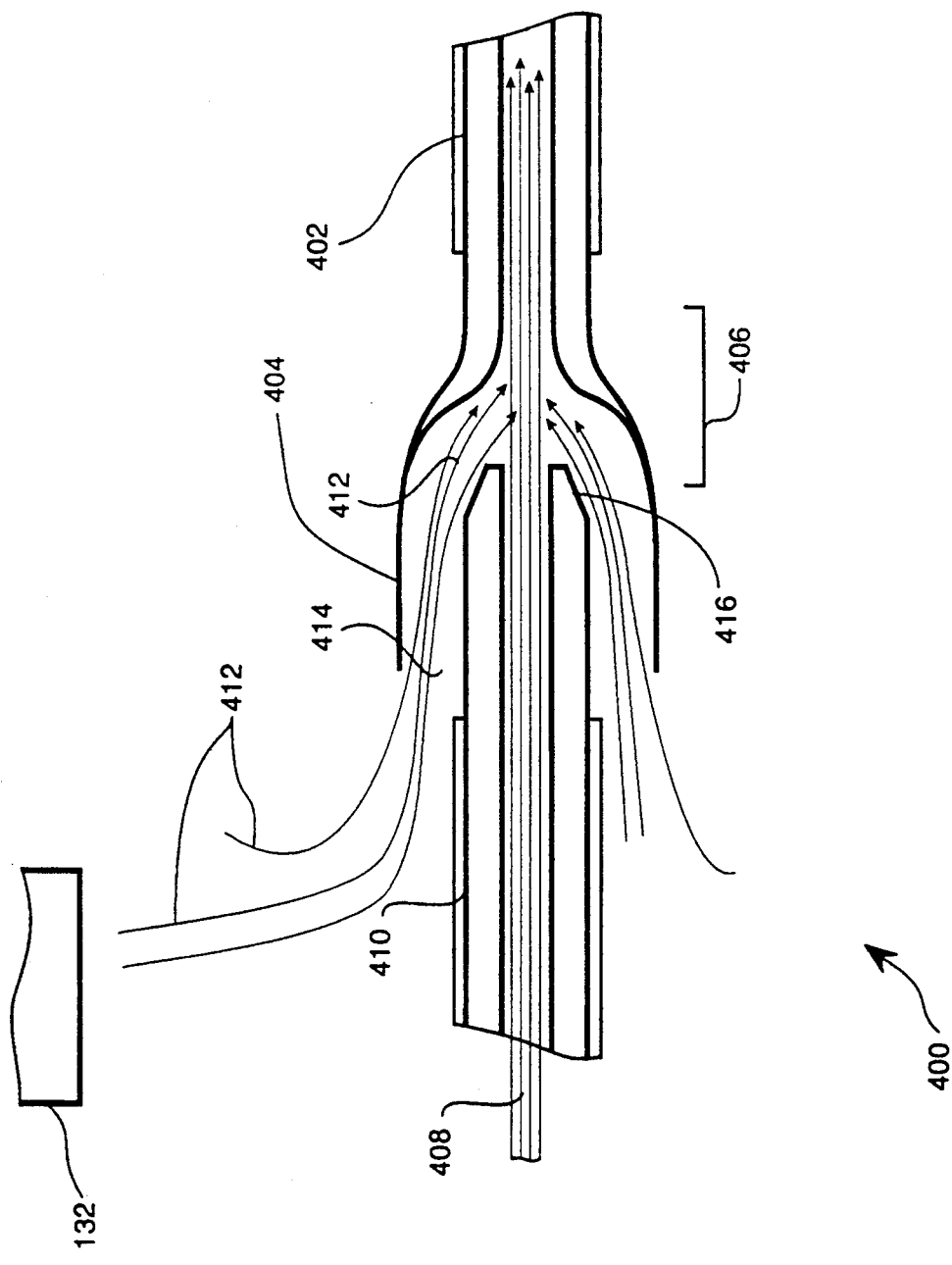
FIG. 4 is a schematic sectional view of an alternative mixing junction in accordance with the present invention.
Figure 5A:
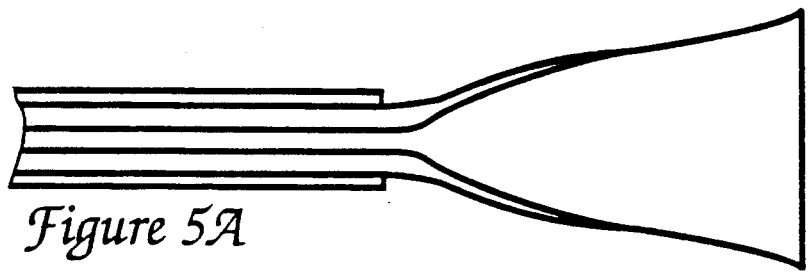
FIGS. 5A–5E are schematic depictions of alternative input ends of mixing capillaries in accordance with the present invention.
Figure 5B:
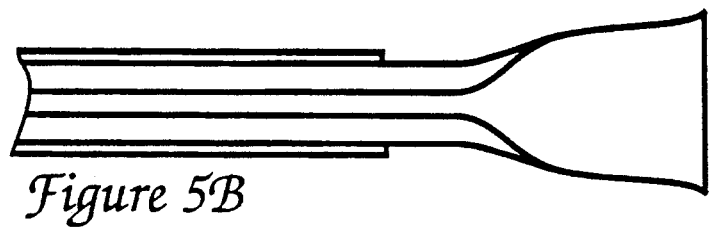
Figure 5C:
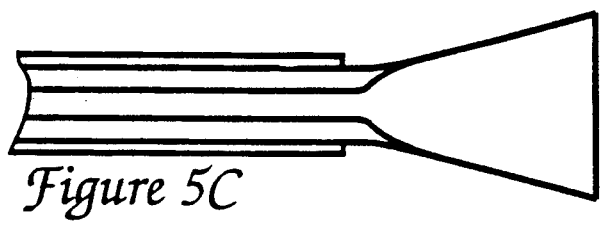
Figure 5D:
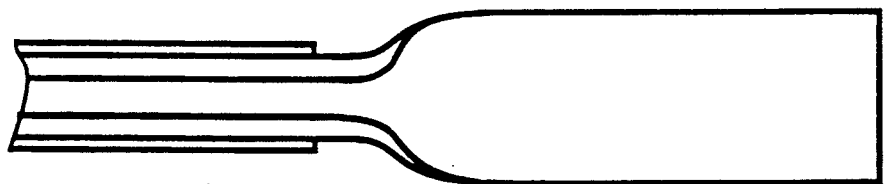
Figure 5E:
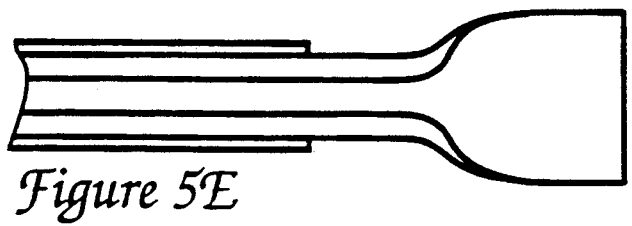

FIG. 4 is a schematic illustration of an alternative mixing junction 400 incorporable in separation system 100 and illustrating the mixing of the fluorogenic reagent with the sample stream. Junction 400 differs from junction 200 of FIG. 2A in the shape of the enlarged input end of the mixing capillary. Junction 400 includes a mixing capillary 402 with a radially enlarged input end 404 and a mixing section 406. Rather than having a flare which increases monotonically toward the input end, input end 404 quickly achieves a maximum diameter which is maintained for a finite longitudinal extent at this input end 404.

Sample stream 408 proceeds through separation capillary 410. Fluorogenic reagent 412 issues from reagent capillary 132, which is positioned orthogonally to capillary 410 and to the direction of flow of sample stream 408. Through diffusion, fluorogenic reagent 402 enters mixing capillary 402 via annular gap 414 between separation output 416 and mixing input 404. Reagent 402 reacts with sample stream 408 in mixing section 406. The results of the reaction are labelled components that can be detected by fluorescence detector 116 of FIG. 1.

FIGS. 5A–5E show various shapes of enlarged bores and flares bores of mixing capillaries provided by the present invention. Depending on the relative dimensions of the separation capillary and the input end of the mixing capillary, the output end of the separation capillary can be left untapered.

Choice of labeling reagents is limited by requirements of compatibility with the selected separation process. Most fluorogenic labels are themselves fluorescent and thus add one or more peaks to detector output. To avoid the spurious fluorescence, the reagent must be completely reacted or excess reagent must be removed before detection. Both these alternatives are highly problematic. It is preferable to use fluorogenic labeling reagents that, like OPA, are not themselves fluoroscent until they react with primary amine functions of protein molecules.

The present invention provides for post-separation mixing that is compatible with the following alternative electro-kinetic separation techniques. Capillary polyacrylamide gel electrophoresis uses electrophoretic migration through a gel matrix. Capillary isoelectric focusing distributes sample components by isoelectric point in a pH gradient formed over the length of a capillary. Isotachophoresis distributes sample components by isoelectric mobility. Micellar electro-kinetic capillary chromatography is a form of chromatography which uses a "stationary" phase that is subject to electro-osmotic flow.

In the preferred embodiment, a fluorogenic labeling reagent is added after separation to enhance detection. The present invention accommodates other detection methods and thus the introduction of detection fluids adapted for these detection methods. For example, mass spectrometry can be used to analyze separated components. The present invention can be used to introduce a detection fluid, specifically, a carrier fluid to sweep separated components into a mass spectrometer. These and other variations upon and modifications to the described embodiments are provided for by the present invention, the scope of which is limited only by the following claims.

What is claimed is:

1. A chemical analysis system comprising
   sample path means for defining a longitudinally extending sample path, said sample path means including:
   a separation capillary with an input end and an output end:
   a mixing capillary having an input end and a mixing section:
   a detection section positioned after said mixing section:
   wherein said input end of said mixing capillary is radially enlarged relative to the remainder of said mixing capillary, an inner diameter of said input end of said mixing capillary is larger than an outer diameter of said output end of said separation capillary, and
   said output end of said separation capillary is positioned within said input end of said mixing capillary for defining an annular gap therebetween;
   sample movement means for moving plural components through said separation capillary at respective rates and through said mixing section and into said detection section;
   detection means for detecting said plural components in a detection fluid in said detection section; and
   detection fluid introduction means for introducing the detection fluid into said mixing section via said annular gap so that said detection fluid mixes with said plural components.

2. A chemical analysis system comprising
   sample path means for defining a longitudinally extending sample path, said sample path means including:
   a capillary separation section having a sample input end and an output end:
   a capillary mixing section having an input end:
   a coupling element for coupling between said output end of said capillary separation section and said input end of said capillary mixing section, said coupling element having fluid introduction means for introducing detection fluid into said mixing section for mixing said detection fluid and effluent from said separation section before movement into a detection section,
   said fluid introduction means including a flared input of said capillary mixing section defining an annular gap between said separation section and said mixing section:
   said detection section being positioned along said sample path after said capillary mixing section;
   a detection fluid path coupled to said coupling element for introducing said detection fluid into said coupling element;
   detection means for detecting the presence of at least one sample component in the detection fluid within said detection section; and
   electrode means for establishing an electric field to move said sample component from said separation section toward said detection section.

3. A system as recited in claim 2 wherein said output end of said separation capillary is narrowed relative to the remainder of said separation capillary.

4. A system as recited in claim 2 wherein said input end of said mixing capillary has an inner diameter at least as large as the inner diameter of said separation capillary.

5. A chemical analysis system for separating a sample solution into components, said system comprising:
   sample path means for defining a longitudinally extending sample path and a downstream direction along said sample path, said sample path means including
   a separation capillary having a separation input end and a separation output end, and
   a detection capillary generally downstream relative to said separation capillary, said detection capillary having a detection input end and a detection output end, said detection capillary having a mixing section adjacent to said detection input end and a detection section downstream of said mixing section, said detection capillary being enlarged radially at said detection input end and at said mixing section, said detection input end longitudinally overlapping said separation output end so as to define an annular gap therebetween;
   power supply means for establishing an electric field between said separation input end and said detection output end, said electric field extending across said annular gap;
   fluorogenic reagent introduction means for introducing a fluorogenic reagent into said mixing section through said annular gap so as to react with sample components eluting from said separation output end so as to produce fluorescent labelled sample components; and
   fluorescence detection means for detecting said fluorescent labelled sample components, said detection means being located at said detection section.

* * * * *